United States Patent
Kelly, Jr.

(10) Patent No.: US 12,274,845 B2
(45) Date of Patent: Apr. 15, 2025

(54) OPTIMIZING INITIAL ORGAN PRESERVATION

(71) Applicant: Burnett Stephens Kelly, Jr., Sacramento, CA (US)

(72) Inventor: Burnett Stephens Kelly, Jr., Sacramento, CA (US)

(73) Assignee: Burnett Stephens Kelly, Jr., Sacramento, CA (US)

( * ) Notice: Subject to any disclaimer, the term of this patent is extended or adjusted under 35 U.S.C. 154(b) by 1236 days.

(21) Appl. No.: 16/977,213

(22) PCT Filed: Mar. 4, 2018

(86) PCT No.: PCT/US2018/020821
§ 371 (c)(1),
(2) Date: Sep. 1, 2020

(87) PCT Pub. No.: WO2019/172864
PCT Pub. Date: Sep. 12, 2019

(65) Prior Publication Data
US 2021/0093841 A1    Apr. 1, 2021

(51) Int. Cl.
*A61M 25/10* (2013.01)
*A61M 39/24* (2006.01)

(52) U.S. Cl.
CPC .......... *A61M 25/104* (2013.01); *A61M 39/24* (2013.01); *A61M 2025/1095* (2013.01);
(Continued)

(58) Field of Classification Search
CPC ................ A61M 25/104; A61M 25/10; A61M 25/10185; A61M 25/10186;
(Continued)

(56) References Cited

U.S. PATENT DOCUMENTS 5,466,216 A    11/1995   Brown et al.
6,090,096 A    7/2000    St. Goar et al.
(Continued)

FOREIGN PATENT DOCUMENTS

WO    2016/090498 A1    6/2016

OTHER PUBLICATIONS

Rosenthal, et al., Principles of Multiple Organ Procurement from Cadaver Donors., Annals of Surgery, Nov. 1983.

*Primary Examiner* — Joel M Attey
*Assistant Examiner* — Alexandra Lalonde
(74) *Attorney, Agent, or Firm* — Boulware & Valoir PLLC

(57) ABSTRACT

A sensor module has an arterial catheter connection hub. The sensor module has a perfusion inflow hub coupled through an arterial/portal blood chamber to the arterial catheter connection hub. The sensor module has a venous catheter connection hub. The sensor module has an effluent outflow hub coupled through a venous blood chamber to the venous catheter connection hub. The sensor module has an arterial sensor to sense a parameter of an arterial fluid flowing through the arterial/portal blood chamber. The sensor module has a venous sensor to sense a parameter of a venous fluid flowing through the venous blood chamber. The sensor module has a processor coupled to the arterial sensor and the venous sensor to determine a relationship between the parameter of the arterial fluid sensed by the arterial sensor and the parameter of the venous fluid sensed by the venous sensor.

11 Claims, 6 Drawing Sheets

(52) U.S. Cl.
CPC ............... *A61M 2039/248* (2013.01); *A61M 2205/3306* (2013.01); *A61M 2205/3334* (2013.01); *A61M 2205/3368* (2013.01); *A61M 2205/583* (2013.01); *A61M 2205/587* (2013.01); *A61M 2230/50* (2013.01)

(58) Field of Classification Search
CPC ........ A61M 2230/005; A61M 2230/50; A61M 3/0229; A61M 2025/1095; A61M 2039/248; A61M 2039/2473; A61M 2205/3306; A61M 2205/3334; A61M 2205/3368; A61M 2205/583; A61M 2205/587; A61M 2205/58; A61M 2205/6063; A61M 2205/6081; A61M 39/24; A61M 2210/12; A61M 2210/125; A61M 60/31; A61M 60/00; A61M 60/178; A61M 2025/0001; A61M 2025/0002; A61M 2025/0003; A61M 2025/0031; A61M 2205/33; A61M 2205/3313; A61M 2205/3327; A61M 2205/3331; A61M 2205/3337; A61M 2205/3344; A61M 2205/3351; A61M 2205/3355; A61M 2205/35; A61M 2205/3507; A61M 2205/3546; A61M 2205/3561; A61M 2205/36; A61M 2205/3626; A61M 60/104; A61M 60/109; A61M 60/117; A61M 60/17; A61M 60/174; A61M 60/30; A61M 60/32; A61M 60/33; A61M 60/50; A61M 60/508; A61M 60/515; A61M 60/523; A61M 60/531; A61M 60/585; A61M 60/592; A61M 1/14; A61M 1/153; A61M 1/154; A61M 1/1678; A61M 1/1698; A61M 1/28; A61M 1/285; A61M 1/36; A61M 1/3601; A61M 1/3603; A61M 1/3607; A61M 1/3609; A61M 1/361; A61M 1/3612; A61M 1/3623; A61M 1/3639; A61M 1/3663; A61M 1/369; A61M 1/77; A61M 5/16831; A61M 5/16854; A61M 5/16886; A61M 2005/16868; A61M 2005/16872; A61M 2202/0021; A61M 2202/0413; A61M 25/0097; A61M 39/10; A61M 2039/1083; A61M 2039/1088; A61M 2205/50; A61M 2210/127; A01N 1/0247; A01N 1/02; A01N 1/0205; A01N 1/021; A01N 1/0236; A01N 1/0242; A01N 1/0278; A01N 1/0284

See application file for complete search history.

(56) References Cited

U.S. PATENT DOCUMENTS

| | | | |
|---|---|---|---|
| 6,293,920 B1* | 9/2001 | Sweezer | A61M 25/1011 604/509 |
| 2010/0082016 A1* | 4/2010 | Graham | A61M 1/7413 604/537 |
| 2012/0183945 A1 | 7/2012 | Steen et al. | |
| 2014/0308654 A1* | 10/2014 | Kay | A01N 1/021 435/284.1 |
| 2015/0119724 A1* | 4/2015 | Weber | A61B 5/0261 600/478 |
| 2016/0309707 A1* | 10/2016 | Steen | A01N 1/0226 |
| 2017/0339945 A1* | 11/2017 | Freed | A01N 1/0247 |

* cited by examiner

OPTIMIZING INITIAL ORGAN PRESERVATION

This application claims priority to PCT/US18/20821, filed Mar. 4, 2018 each incorporated by reference in its entirety for all purposes.

BACKGROUND

There are approximately 10,000 deceased organ donation operations performed for the 120,500 patients awaiting organ transplant in the US. This does not include the 1000-1500 donations after cardiac death operations that also occur annually. An estimated 90% of donation procedures require an abdominal incision, isolation of the infra renal aorta, and cannulation of the aorta and most times the portal vein for retrograde perfusion and preservation of the abdominal viscera. The entire blood volume is evacuated and the organs are cooled with a combination of topical ice and cold preservation solution to an ideal temperature of less than 4-6 degrees C. to achieve cellular metabolic arrest. During the abdominal organ preservation process the amount of preservation solution is estimated based on clearing blood from the venous effluent and the patient's lean body weight as a surrogate for the total blood volume. After completing infusion of preservation solution, the organs are systematically dissected and removed from the body. Following organ packaging in fresh preservation solution, transport, and removal of the recipient's diseased organ, the donor organ is reperfused in the recipient, re-initializing the organ's cellular metabolism and effectively ending the cold ischemia time.

The cold storage preservation process makes several assumptions:
1. The final core temperature of the organ is less than 6° C.
2. The preservation solution infusion was the appropriate volume to achieve cellular metabolic stasis.
3. The blood volume was effectively removed from the organ limiting the amount of potential immunogenicity imposed by retained red blood cells (RBC's) and immunocytes.
4. Cellular metabolism has been arrested, and the organ remains in cellular stasis throughout the cold storage process.

With these assumptions, the cold storage process and surgical dissection produces several problems:
1. There is no mechanism to consistently measure or estimate the core organ temperature during each operation.
2. There is no mechanism to accurately measure or estimate the appropriate donor-specific preservation infusion volume. This is critical; particularly for sensitive tissues like the biliary epithelium or intestinal mucosa.
3. There is no mechanism to quantify the effectiveness of blood removal from the organs.
4. There is no mechanism to measure the effectiveness of cellular metabolism at the initiation of preservation and prior to reperfusion.
5. The proximal and distal vasculature isolation dissection is time consuming, requires encircling vascular clamping of the supraceliac aorta, and ideally, evacuation of blood volume into the chest.

DETAILED DESCRIPTION

Premise of the Initial Organ Preservation System (TOPS)

The general premise of the iOPS is to provide a consistent, efficient, and expeditious technique and mechanism for cannulating the central arterial inflow and venous outflow (aorta and vena cava) to effectively isolate and perfuse the intra-abdominal organs, actively evacuate the blood in the organs, measure the effluent temperature, and measure the fluid colorimetric spectrum differential of blood entering/exiting organs to estimate effectiveness of organ flush (adequate volume of preservation solution). There is no crossclamp or suprahepatic dissection required. Because the blood is actively evacuated from the body, the preservation solution will be "pulled" through the organs leading to more rapid core cooling. This system also allows effluent sampling to measure biomarkers of arrested cellular metabolism in real-time. Collectively, this additional data serves as another tool to evaluate organs-expanding the pool of donor organs yielding good outcomes for transplant recipients.

Product Design

Arterial Balloon Catheter

Figure 1:
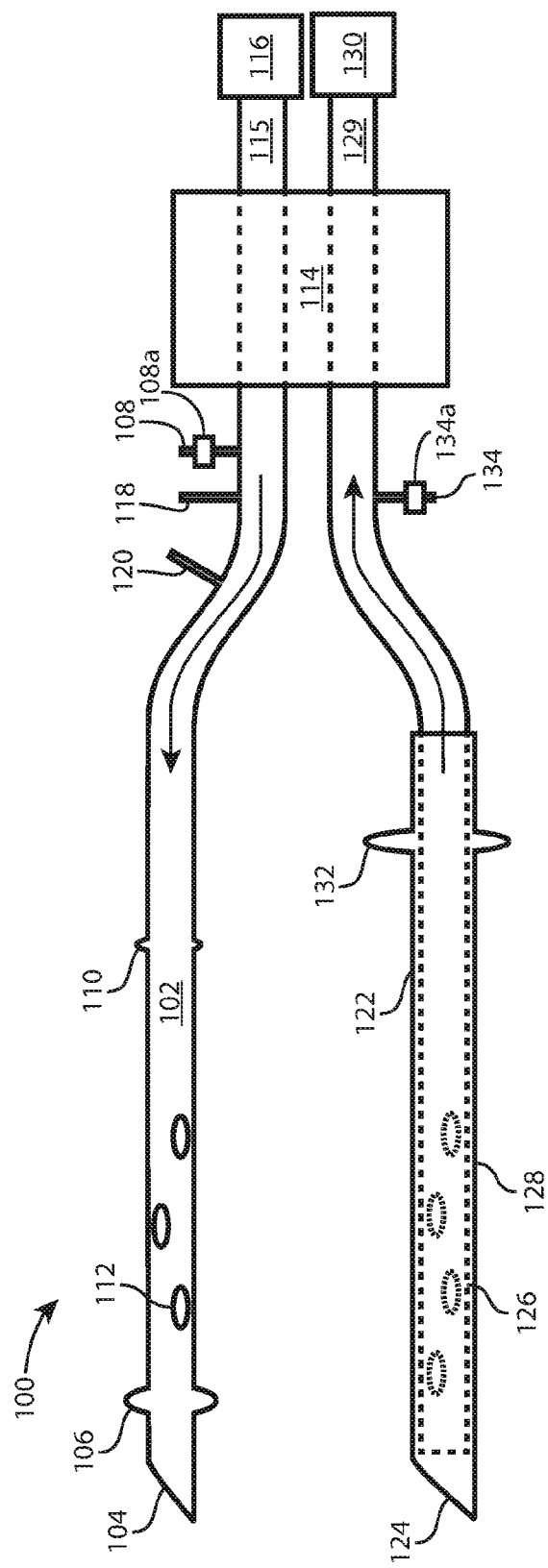
FIG. 1 is a schematic representation of the Initial Organ Preservation System (TOPS).

FIG. 1, which is a schematic representation of the iOPS 100, includes an arterial balloon catheter 102. The arterial balloon catheter 102 is a 10-18Fr Silastic catheter that, in one or more embodiments, ranges from 10-35 cm long. The distal tip 104 is beveled to facilitate arteriotomy cannulation. Approximately 2 centimeters (cm) below the tip is a durable arterial occlusion balloon 106 that inflates to occlude the aorta via a catheter tip syringe ball-valve port 108, which includes a ball valve (schematically represented by block 108a) to open and close the flow of air to inflate the arterial occlusion balloon 106. The arterial balloon catheter 102 includes a proximal flange 110 to mark the 12.5 cm to 30.5 cm position of the distal arterial occlusion balloon 104 of the arterial balloon catheter 102 as well as to promote secure positioning of the arterial balloon catheter 102 and occlusion of the arteriotomy around the arterial balloon catheter 102 by ligation. Along the length of the arterial balloon catheter 102 between the proximal flange 110 and the arterial occlusion balloon 106 are side holes 112 (only one is labeled) for perfusion of the abdominal organs. A sensor module 114 includes a temperature probe and a color detector (discussed below in reference to FIGS. 2A-2D) that extend into the inner lumen of the catheter 102. The arterial balloon catheter 102 feeds through the sensor module 114 (as indicated by the dashed lines) and a distal perfusion tubing 115 to a source of perfusion fluid 116. The arterial balloon catheter 102 includes an access port 118, for sampling fluids from or infusion of therapeutic and/or diagnostic substances into the catheter 102, and a portal port 120, for connection of separate tubing to infuse the portal venous system. The arterial balloon catheter 102 and the arterial occlusion balloon 106 are coated with a heparin-like compound to deter thrombus formation.

Venous Catheter

The iOPS 100 includes a venous catheter 122. The venous catheter 122 is, in one or more embodiments, a 12-18 Fr silastic catheter that is 5-15 cm long with a beveled firm rubber tip 124 for ease of cannulation of infrarenal vena cava or through a supradiaphragmatic venotomy. The venous catheter 122 includes an inner catheter 126 within an outer catheter 128. The outer catheter 128 is a firm catheter. The inner catheter 126 is a rigid fenestrated catheter that is connected through the sensor module 114 (indicated by the dashed lines through the sensor module 114) and suction tubing 129 to a standard operating room external suction device 130, which facilitates evacuating the perfusion fluids from the body. The combination of the firm outer catheter 128 and the rigid inner catheter 126 allows for active evacuation of the lower body and visceral blood volume without collapsing the vena cava. Approximately 2 cm distal to the vein insertion site is a venous occlusion balloon 132 that can be inflated to occlude the venous outflow, and maintain the patency of the vein adjacent to the suction catheter. The ideal positioning of the distal end of the outer catheter is inferior to the inferior edge of the liver. The venous occlusion balloon 132 can be inflated and deflated by way of a venous catheter balloon inflation port and ball valve 134, which includes a ball valve (schematically represented by block 134*a*) to open and close the flow of air to inflate the venous occlusion balloon 132. The sensor module 114 (discussed in more detail below in connection with FIGS. 2A-2D) includes a temperature probe fitted near the distal end the inner cannula to measure the temperature of the core visceral effluent. The venous catheter 122 and venous occlusion balloon 132 are coated with a heparin-like compound to deter thrombus formation.

Note that the portal cannulation and preservation is the standard approach utilizing a separate catheter tubing that attaches to the sensor module or can be operated as an independent perfusion line separate from the iOPS.

Sensor Module and Monitor Module

Figure 2A:
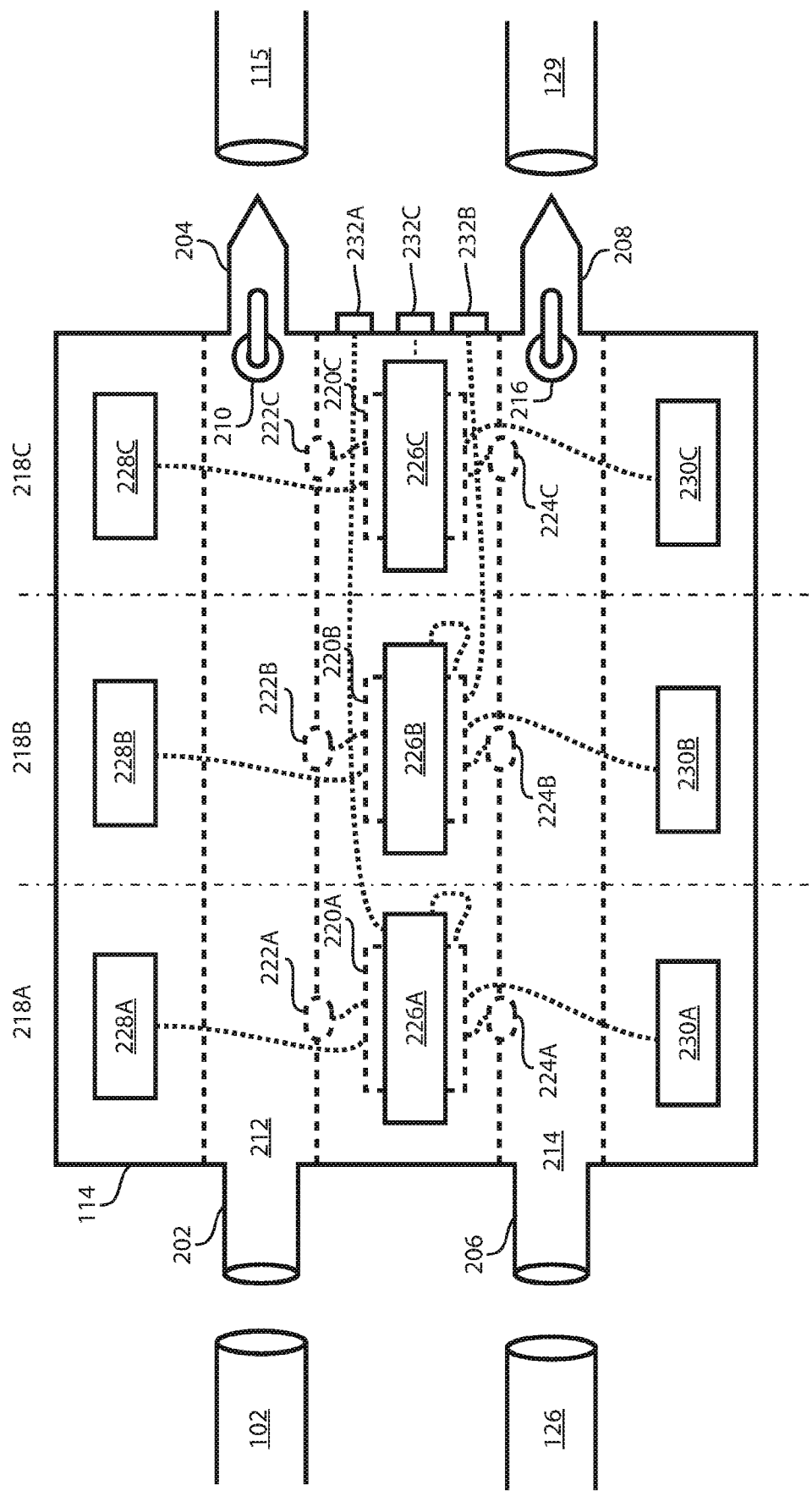
FIG. 2A is a block diagram of the iOPS.

FIG. 2A is a diagram showing the physical layout of the sensor module 114. The sensor module 114 is used to determine when the organs have been adequately flushed of RBC's and the core temperature of the effluent is below 6° C. In one or more embodiments, the sensor module 114 is a lightweight disposable device.

The sensor module 114 includes an arterial catheter connection hub 202 that can be coupled to the arterial balloon catheter 102, a perfusion inflow hub 204 that can be coupled to the distal perfusion tubing 115, a venous catheter connection hub 206 that can be coupled to the inner catheter 126 of the venous catheter 122 (see FIG. 1), and an effluent outflow hub 208 that can be coupled to suction tubing 129. Perfusion fluid flows from source of perfusion fluid 116 (shown in FIG. 1), through the perfusion inflow hub 204, through a perfusion shut-off valve with air bubble vent 210, through an arterial/portal blood chamber 212, through the arterial catheter connection hub 202, through the arterial balloon catheter 102, and into the body for perfusion. Returning perfusion fluid containing bodily fluids flows through the inner catheter 126 of the venous catheter 122, through the venous catheter connection hub 206, through a venous blood chamber 214, through a suction shut-off valve with air bubble vent 216, through the effluent outflow hub 208, through the suction tubing 129, and to the pump 130.

The sensor module 114 includes multiple sensors for measuring various parameters of the fluids flowing through the arterial/portal blood chamber 212 and the venous blood chamber 214. The theory behind the operation of the sensor module 114 is that differences in the measured properties of the fluid flowing through the arterial/portal blood chamber 212 and the measured properties of the fluid flowing through the venous blood chamber 214 can be analyzed to determine that perfusion is complete, with the surgeon making the final determination.

For example, if the temperature of the fluid in the venous blood chamber 214 is 4° C., that likely means the organs in the body have reached goal temperature, as described in the background. Further, the fluid in the venous blood chamber 214 should be relatively clear of RBCs when perfusion is completed. This can be determined by measuring the difference in color between the fluid in the arterial/portal blood chamber 212 and the fluid in the venous blood chamber 214. Other similar parameters can be measured and analyzed to determine if perfusion should be deemed complete.

Some of the parameters can be measured with sensors that are inserted into the fluid flowing through the arterial/portal blood chamber 212 and the venous blood chamber 214. Temperature and flow rate are examples of such parameters. Other parameters can be measured with sensors that do not come into direct contact with the fluid in the arterial/portal blood chamber 212 and the fluid in the venous blood chamber 214. The color sensors described below are examples.

In one or more embodiments, the sensor module includes three sensor sets 218A-C (separated in FIG. 2A by vertical dot-dashed lines).

Sensor set 218A includes a processor 220A (the elements of the sensor module 114 not on the surface are shown in dashed lines), which may be a microprocessor, a programmable logic array (PLA), digital circuitry, analog circuitry, or a combination of these. The sensor set 218A includes an arterial sensor 222A and a venous sensor 224A that measure a property (such as temperature, color, flow, or flow resistance) of the arterial/portal blood chamber 212 and the venous blood chamber 214, respectively. The arterial sensor 222A and the venous sensor 224A are connected to the processor 220A by a wire represented by dashed lines in FIG. 2A. The two sensors 222A and 224A may be single sensors, such as a temperature sensor, or they may include more than one device, such as with the color sensors described in connection with FIGS. 2B-2D below. The two sensors 222A and 224A may each be of the type that are inserted into the fluid flowing through the fluid in the arterial/portal blood chamber 212 and the fluid in the venous blood chamber 214 or they may each may be of the type that do not come into direct contact with the fluid in the arterial/portal blood chamber 212 and the fluid in the venous blood chamber 214, or the two sensors 222A and 224A may be different in this respect.

Sensor set 218A includes a power source 226A, which may include a solar panel that uses the light that falls on the sensor module 114 to generate electricity, a thermoelectric power generator that uses the difference in temperature between the fluid flowing in the arterial/portal blood chamber 212 and the venous blood chamber 212 to generate electricity, a external power source (not shown), or a combination of these or similar power sources to provide power to the processor 220A and any other parts in the sensor module 114 that need power.

Sensor set 218A includes an input/output device 228A. In one or more embodiment, the input/output device 228A is a display that displays (a) data measured by the sensor 222A, such as temperature, color, flow, flow resistance or similar measured parameter, (b) information determined from calculations made using the data measured by the sensor 222A, such as the degree of completeness of perfusion based on the data measured by the sensor 222A, etc., (c) elapsed time since the perfusion began, (d) other similar information. In one or embodiments, the input/output device 228A is an input device, such as a switch, an array of switches, or a similar input device, by which a user can input information to the processor 220A, such as a "start perfusion" command, set-up commands (such as configuration information), flow rates, flow resistance, temperature thresholds, or the like. In one or more embodiments, the input/output device 228A is a combination input and output device that includes a pressable switch with a small status display on the switch face that can be read and written to by the processor 220A. For example, the small status display may begin the process with a "BEGIN?" message, change to alternating between a display of the time elapsed since the switch was pressed and a display of data collected from sensor 222A or information calculated from that data after the switch is depressed, and change to a "COMPLETE" message when certain parameters of the data collected from the sensor 222A or the information calculated from that data fall within specified ranges.

The sensor set 218A includes an input/output device 230A that is similar in functionality to the input/output device 228A.

The sensor set 218A includes a data port 232A by which the processor 220A can be remotely controlled and/or by which data can be remotely read from the processor 220A. For example, data may be read from the processor 220A that reflects the data collected by sensors 222A and 224A or the information calculated from that data and may be used by a remote system to analyze the success of the perfusion. For example, such data may be analyzed to determine how long it took for the effluent perfusion fluid to reach the desired temperature and conclusions may be drawn from that information as to the quality of the perfusion.

Sensor set 218B includes a processor 220B (the elements of the sensor module 114 not on the surface are shown in dashed lines), which may be a microprocessor, a programmable logic array (PLA), digital circuitry, analog circuitry, or a combination of these. The sensor set 218B includes an arterial sensor 222B and a venous sensor 224B that measure a property (such as temperature, color, flow, or flow resistance) of the arterial/portal blood chamber 212 and the venous blood chamber 214, respectively. The arterial sensor 222B and the venous sensor 224B are connected to the processor 220B by a wire represented by dashed lines in FIG. 2A. The two sensors 222B and 224B may be single sensors, such as a temperature sensor, or they may include more than one device, such as with the color sensors described in connection with FIGS. 2B-2D below. The two sensors 222B and 224B may each be of the type that are inserted into the fluid flowing through the fluid in the arterial/portal blood chamber 212 and the fluid in the venous blood chamber 214 or they may each may be of the type that do not come into direct contact with the fluid in the arterial/portal blood chamber 212 and the fluid in the venous blood chamber 214, or the two sensors 222B and 224B may be different in this respect.

Sensor set 218B includes a power source 226B, which may include a solar panel that uses the light that falls on the sensor module 114 to generate electricity, a thermoelectric power generator that uses the difference in temperature between the fluid flowing in the arterial/portal blood chamber 212 and the venous blood chamber 212 to generate electricity, a external power source (not shown), or a combination of these or similar power sources to provide power to the processor 220B and any other parts in the sensor module 114 that need power.

Sensor set 218B includes an input/output device 228B. In one or more embodiment, the input/output device 228B is a display that displays (a) data measured by the sensor 222B, such as temperature, color, flow, or similar measured parameter, (b) information determined from calculations made using the data measured by the sensor 222B, such as the degree of completeness of perfusion based on the data measured by the sensor 222B, etc., (c) elapsed time since the perfusion began, (d) other similar information. In one or embodiments, the input/output device 228B is an input device, such as a switch, an array of switches, or a similar input device, by which a user can input information to the processor 220B, such as a "start perfusion" command, set-up commands (such as configuration information), flow rates, flow resistance, temperature thresholds, or the like. In one or more embodiments, the input/output device 228B is a combination input and output device that includes a pressable switch with a small status display on the switch face that can be read and written to by the processor 220B. For example, the small status display may begin the process with a "BEGIN?" message, change to alternating between a display of the time elapsed since the switch was pressed and a display of data collected from sensor 222B or information calculated from that data after the switch is depressed, and change to a "COMPLETE" message when certain parameters of the data collected from the sensor 222B or the information calculated from that data fall within specified ranges.

The sensor set 218B includes an input/output device 230B that is similar in functionality to the input/output device 228B.

The sensor set 218B includes a data port 232B by which the processor 220B can be remotely controlled and/or by which data can be remotely read from the processor 220B. For example, data may be read from the processor 220B that reflects the data collected by sensors 222B and 224B or the information calculated from that data and may be used by a remote system to analyze the success of the perfusion. For example, such data may be analyzed to determine how long it took for the effluent perfusion fluid to reach the desired temperature and conclusions may be drawn from that information as to the quality of the perfusion.

Sensor set 218C includes a processor 220C (the elements of the sensor module 114 not on the surface are shown in dashed lines), which may be a microprocessor, a programmable logic array (PLA), digital circuitry, analog circuitry, or a combination of these. The sensor set 218C includes an arterial sensor 222C and a venous sensor 224C that measure a property (such as temperature, color, flow, or flow resistance) of the arterial/portal blood chamber 212 and the venous blood chamber 214, respectively. The arterial sensor 222C and the venous sensor 224C are connected to the processor 220C by a wire represented by dashed lines in FIG. 2A. The two sensors 222C and 224C may be single sensors, such as a temperature sensor, or they may include more than one device, such as with the color sensors described in connection with FIGS. 2B-2D below. The two sensors 222C and 224C may each be of the type that are inserted into the fluid flowing through the fluid in the arterial/portal blood chamber 212 and the fluid in the venous blood chamber 214 or they may each may be of the type that do not come into direct contact with the fluid in the arterial/portal blood chamber 212 and the fluid in the venous blood chamber 214, or the two sensors 222C and 224C may be different in this respect.

Sensor set 218C includes a power source 226C, which may include a solar panel that uses the light that falls on the sensor module 114 to generate electricity, a thermoelectric power generator that uses the difference in temperature between the fluid flowing in the arterial/portal blood chamber 212 and the venous blood chamber 212 to generate electricity, a external power source (not shown), or a combination of these or similar power sources to provide power to the processor 220C and any other parts in the sensor module 114 that need power.

Sensor set 218C includes an input/output device 228C. In one or more embodiment, the input/output device 228C is a display that displays (a) data measured by the sensor 222C, such as temperature, color, flow, flow resistance, or similar measured parameter, (b) information determined from calculations made using the data measured by the sensor 222C, such as the degree of completeness of perfusion based on the data measured by the sensor 222C, etc., (c) elapsed time since the perfusion began, (d) other similar information. In one or embodiments, the input/output device 228C is an input device, such as a switch, an array of switches, or a similar input device, by which a user can input information to the processor 220C, such as a "start perfusion" command, set-up commands (such as configuration information), flow rates, temperature thresholds, or the like. In one or more embodiments, the input/output device 228C is a combination input and output device that includes a pressable switch with a small status display on the switch face that can be read and written to by the processor 220C. For example, the small status display may begin the process with a "BEGIN?" message, change to alternating between a display of the time elapsed since the switch was pressed and a display of data collected from sensor 222C or information calculated from that data after the switch is depressed, and change to a "COMPLETE" message when certain parameters of the data collected from the sensor 222C or the information calculated from that data fall within specified ranges.

The sensor set 218C includes an input/output device 230C that is similar in functionality to the input/output device 228C.

The sensor set 218C includes a data port 232C by which the processor 220C can be remotely controlled and/or by which data can be remotely read from the processor 220C. For example, data may be read from the processor 220C that reflects the data collected by sensors 222C and 224C or the information calculated from that data and may be used by a remote system to analyze the success of the perfusion. For example, such data may be analyzed to determine how long it took for the effluent perfusion fluid to reach the desired temperature and conclusions may be drawn from that information as to the quality of the perfusion.

The arterial sensors 222A-C and the venous sensors 224A-C may include a temperature sensor, such as a thermistor or thermocouple, that measures the temperature of the fluid in the arterial/portal blood chamber 212 or the venous blood chamber 214, a color sensor that measures the color of the fluid in the suction tubing 136, and a color sensor that measures the color of the fluid in the arterial/portal blood chamber 212 or the venous blood chamber 214 (such as those illustrated in FIGS. 2B, 2C, and 2D, described below), a flow sensor that measures the rate of flow of fluid through the arterial/portal blood chamber 212 or the venous blood chamber 214, or another type of sensor that measures another parameter regarding fluid in the arterial/portal blood chamber 212 or the venous blood chamber 214.

Figure 2B:
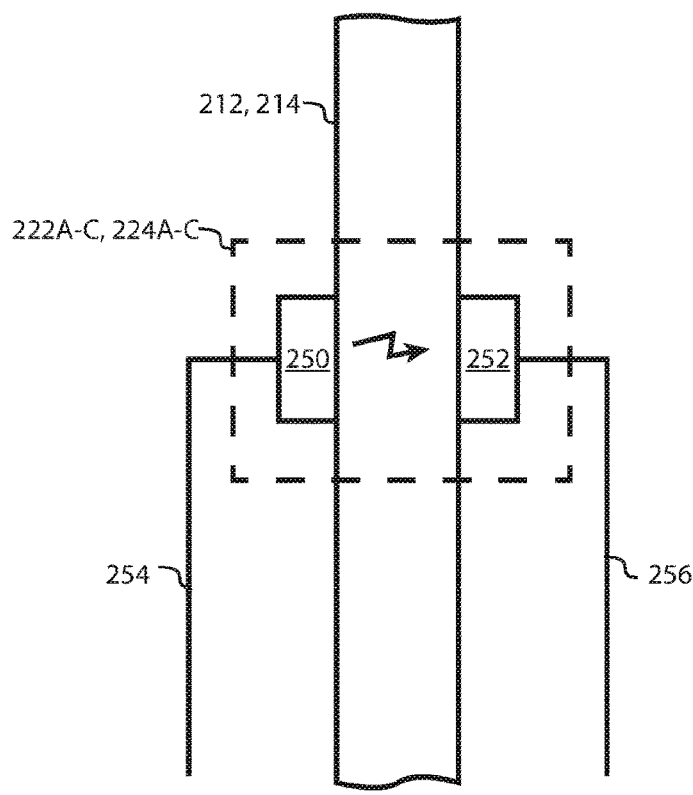
FIG. 2B is a block diagram of a color sensor.

FIG. 2B is a block diagram of a color sensor, such as might be used for arterial sensors 222A-C and/or venous sensors 224A-C. In one embodiment, a color sensor includes a source of light 250 and a light detector 252 disposed on opposite sides of the arterial/portal blood chamber 212 or the venous blood chamber 214.

The source of light 250 may be a light emitting diode (LED) and the light detector may be a photo detector. The source of light 250 emits light (represented by the lightning bolt in FIGS. 2B-2D) and the light detector 252 may be positioned to detect light from the source of light 250 that passes through the arterial/portal blood chamber 212 or the venous blood chamber 214 and any fluid therein to produce a signal representing the strength or intensity of that light. The light emitted by the source of light 250 may have a wavelength such that RBCs absorb the light in the fluid passing through the arterial/portal blood chamber 212 or the venous blood chamber 214. As a result, the greater the concentration of RBCs in the fluid the smaller the signal produced by the light detector 252.

Figure 2C:
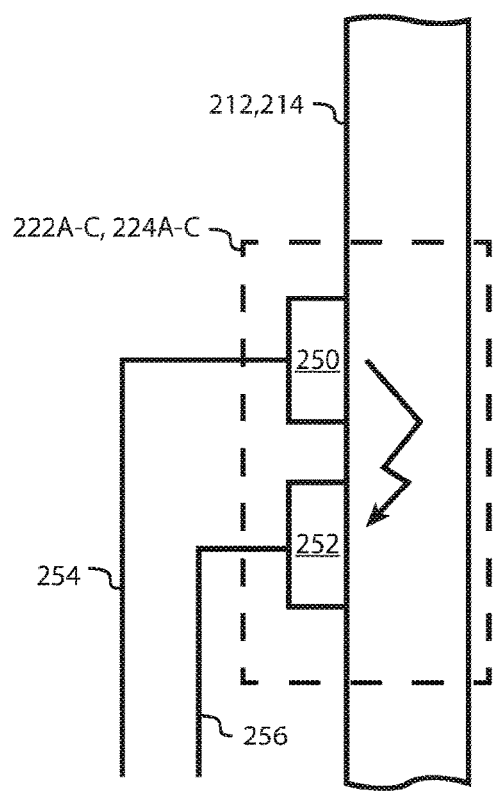
FIG. 2C is a block diagram of a color sensor.

In another embodiment, illustrated in FIG. 2C, which is a block diagram of a color sensor, the source of light 250 and light detector 252 are situated on the same side of the arterial/portal blood chamber 212 or the venous blood chamber 214 and the light produced by the source of light 250 has a wavelength such that the light reflects off RBCs in the fluid. As a result, the greater the concentration of RBCs in the fluid the larger the signal produced by the light detector 252.

The source of light 250 may be controlled by control line 254, which is part of the wire connecting the processor 220A-B to the arterial sensors 222A-C and/or venous sensors 224A-C. The controls may include turning the source of light 250 on or off, adjusting the wavelength or intensity of the light produced by the source of light 250, and other similar controls.

The light detector 252 may be controlled by control line 256, which is part of the wire connecting the processor 220A-B to the arterial sensors 222A-C and/or venous sensors 224A-C. The control line 256 may include the signal from the light detector 254 that indicates the strength or intensity of the light detected by the light detector 252. The controls may include turning the light detector on or off and other similar controls.

The source of light 250 may be an ultraviolet LED that emits light at a wavelength of approximately 395 nanometers (nm), which is a wavelength at which blood is absorptive. An example of such an LED is the SM1206UV-395-1L manufactured by Bivar. Other LED colors, such as blue and green LEDs, can also be used. Such arrangements would be useful in the embodiment illustrated in FIG. 2B.

The light detector 252 may be a photodiode that is responsive to ultraviolet light, such as the EPD-365-0-0.9 manufactured by Roithner LaserTechnik GmbH. The light detector 254 may be chosen to be responsive to light emitted by the source of light 250.

The source of light 250 may be a red LED that emits light at a wavelength of approximately 660 nm, which is a wavelength at which blood is less absorptive. An example of such an LED is the BOO6G6QXSO manufactured by Bluecell. Such arrangements would be useful in the embodiment illustrated in FIG. 2C.

The light detector 252 may be a photodiode that is responsive to red light, such as the 057-14-21-011 manufactured by Luna Optoelectronics.

The arterial sensors 222A-C and/or venous sensors 224A-C may be a combination of the embodiments illustrated in FIG. 2B and FIG. 2C.

Figure 2D:
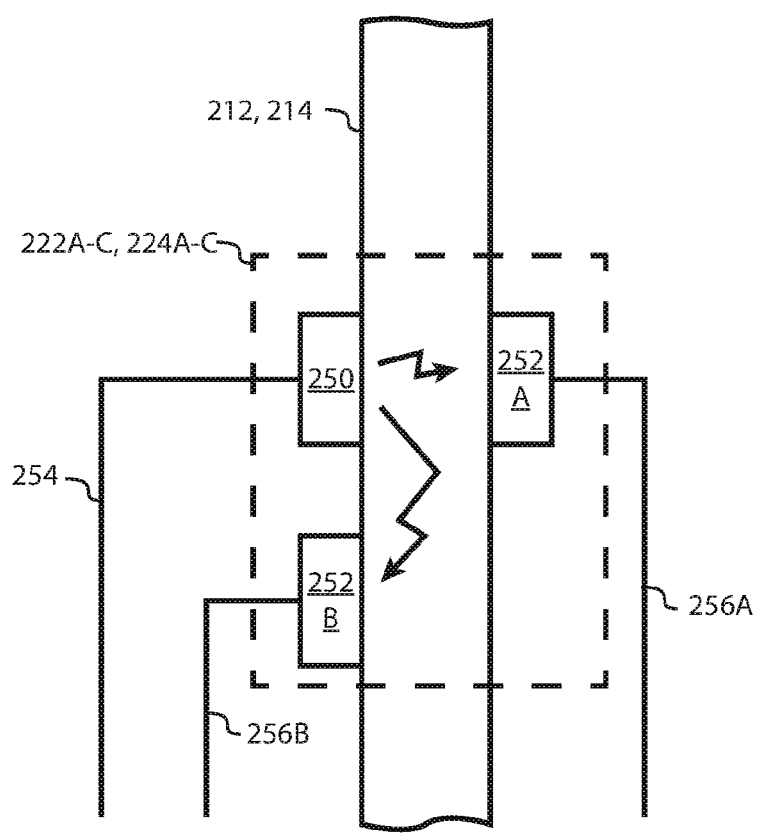
FIG. 2D is a block diagram of a color sensor.

FIG. 2D is an example of an arterial sensors 222A-C and/or venous sensors 224A-C that is a combination of the embodiments illustrated in FIGS. 2B and 2C. In this embodiment, the source of light 250 may be a multi-color LED. An example of such a multi-color LED is the YSL-R596CR3G4B5C-C10 manufactured by CHINA YOUNG SUN LED TECHNOLOGY CO., LTD, which includes a red LED, a green LED, and a blue LED in a single package. The source of light 250 may be controlled by control line 254, which is part of wire 116, to select the color or colors of the multi-color LED to illuminate.

The arterial sensors 222A-C and/or venous sensors 224A-C may include a light detector 252A, which may be a photodiode that is responsive to ultraviolet light, and a light detector 252B, which may be a photodiode that is responsive to red light. The combination of source of light 250 and light detector 252A operates in the same way as the combination described above in connection with FIG. 2B and the combination of source of light 250 and light detector 252B operates in the same way as the combination described above in connection with FIG. 2C.

In one example of use, the control line 254 is used to energize for a first predetermined period of time an ultraviolet LED in the source of light 250 and the light detector 252A is used to take a reading on the amount of light penetrating the arterial/portal blood chamber 212 or the venous blood chamber 214 to the light detector 252A. The control line 254 is then used to de-energize the ultraviolet LED in the source of light 250 and energize for a second predetermined period of time a red LED in the source of light 250 and the light detector 252B is used to take a reading on the amount of light reflecting from the fluid in the arterial/portal blood chamber 212 or the venous blood chamber 214. The two readings may then be used separately or together to determine the color of the fluid in the distal perfusion tubing 134 or suction tubing 136.

Returning to FIG. 2A, the sensor module 114 includes one or more processors 220A-C, discussed above, that connect to the arterial sensors 222A-C and/or venous sensors 224A-C, and process signals from those sensors into data representing the temperature and color of the fluid in the arterial/portal blood chamber 212 or the venous blood chamber 214. One or more of the processors 220A-C perform a spectrophotometer process and determines the color differential between the inflow preservation solution (clear) based on the data from one or more of the arterial sensors 222A-C configured as a color sensor and the effluent solution (bloody) based on data from one or more of the venous sensors 224A-C configured as a color sensor and displays the result as a ratio on one or more of the displays 228A-C, 230A-C. The processor determines the temperature difference between the inflow preservation solution based on the data from one or more of the arterial sensors 222A-C configured as a temperature sensor and the effluent solution based on data from one or more of the venous sensors 224A-C configured as a temperature sensor and displays the result as a ratio on one or more of the displays 228A-C, 230A-C. Once the color and temperature differential readouts plateau or reach a value of 1 (or approximately 1, where "approximately" in this context means with 1 percent of 1, within 5 percent of 1, or within 10 percent of 1), and the effluent temperature is less than a threshold temperature (e.g., 6° C.), the preservation is deemed complete. In one or more embodiments, one or more of the processors 220A-C lights a "complete" light to show completion of the preservation. In one or more embodiments, one or more of the processors 220A-C communicates remotely (over a local area network, a wide area network, and/or the Internet) with a controller (not shown) by which the system can be controlled, monitored, and data captured. The preservation process can be manually arrested prior to or after the "complete" indicator light registers.

Operative Process—Device Use

For the brain-deceased organ donation operation: Following standard OR practices for patient positioning, identification, and verification of donor ABO and serologies; a midline incision from xiphoid to pubic symphysis is performed. The abdomen is entered under direct vision. The umbilical ligament is ligated and the falciform ligament dissected up to the left and right coronary ligaments. The right colon and duodenum are mobilized and medialized to expose the infrahepatic cava. The root of the small bowel mesentery is dissected all the way to the ligament of Treitz and underlying inferior mesenteric vein. The infrarenal aorta is identified and dissected free from the surrounding tissue. Localized proximal and distal control is obtained with umbilical tapes. The infrarenal vena cava is isolated in a similar fashion directly adjacent to the aortic isolation. After systemic anticoagulation, the distal aorta and vena cava are ligated. The distal aorta and immediately adjacent the inferior vena cava (IVC) are cannulated with the respective aortic and venous catheters. The respective catheters are secured into position with the umbilical tapes. The arterial catheter is inserted retrograde through an aortotomy and advanced until the flange is seated in the aorta. The catheter is secured into position occluding the opening around the catheter. With the suction valve turned off, the venous catheter is inserted into the infrarenal vena cava adjacent to the aortotomy, implementing the same steps as the arterial catheter placement. Once both catheters are secured into position, any air within the perfusion or venous suction chambers are systematically evacuated via the respective valves prior to connecting the perfusion and suction tubing. The arterial perfusion and venous suction catheters are attached to the sensor module with the respective valves in the off position to prevent blood loss and introduction of air to the circuit. The proximal position of the respective catheters is verified prior to inflating the occlusion balloons.

Figure 3:
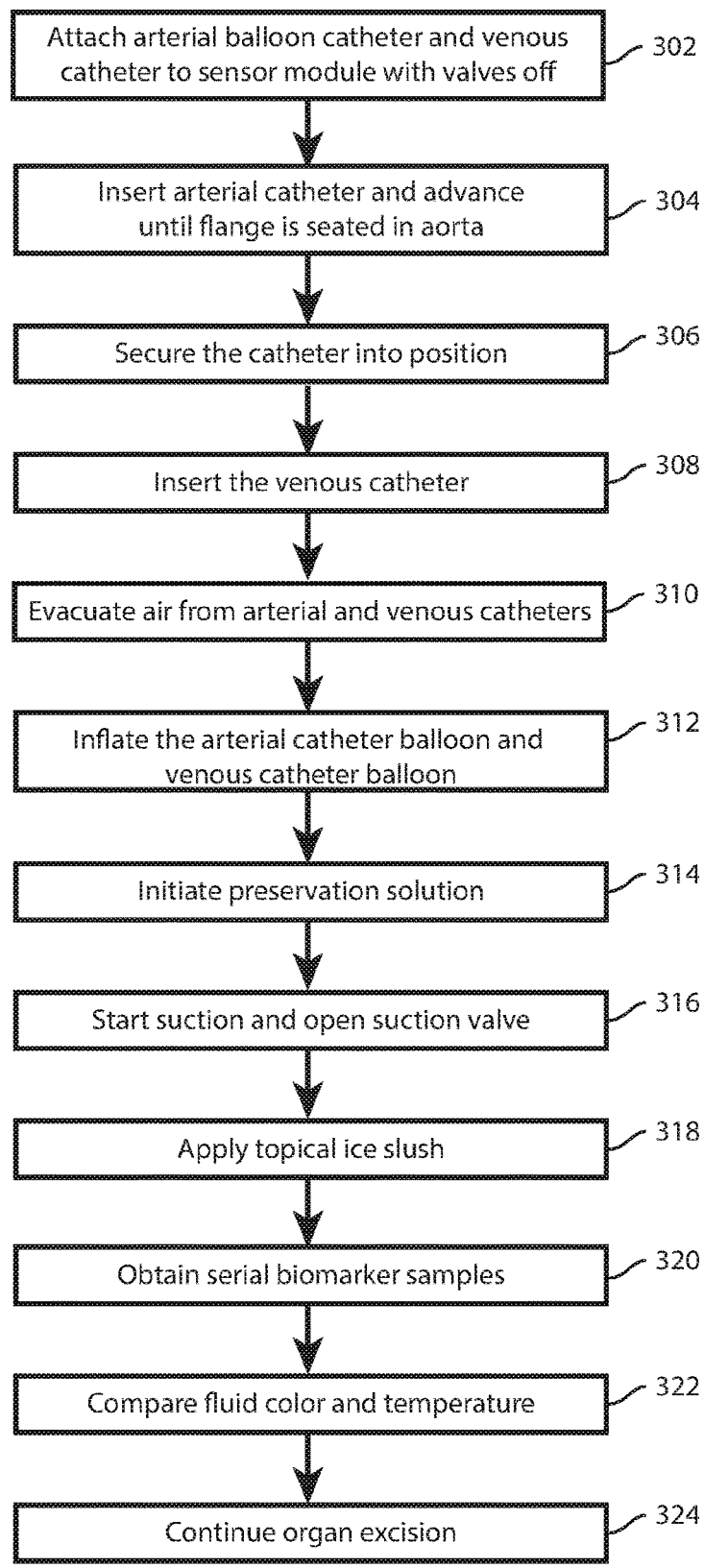
FIG. 3 is a flow chart of the preservation process.

The preservation then begins, as illustrated in FIG. 3, which is a flow chart of the preservation process. The arterial balloon catheter 102 for perfusion and venous catheter 122 for suction are attached to the sensor module 114 with the respective valves 108a, 134a in the off position to prevent blood loss and introduction of air to the circuit (block 302). The arterial catheter is inserted retrograde through an aortotomy and advanced until the flange is seated in the aorta (block 304). The catheter is secured into position occluding the opening around the catheter (block 306). With the suction valve turned off, the venous catheter is inserted in the same steps as the artery catheter (block 308). Once both catheters are secured into position, any air within the perfusion or venous suction chambers is systematically evacuated via the respective valves prior to connecting the perfusion and suction tubing (block 310). When it is time for cross-clamp (initiation of organ preservation), the arterial catheter balloon and the venous catheter balloons are inflated (block 312) and the preservation solution is initiated (block 314). The suction valve on the sensor module is then turned to the suction position to evacuate blood from the abdominal viscera. No cardiotomy is required, and is not recommended. A standard high-volume suction device is recommended for venous blood evacuation (block 316). Topical ice slush can be applied to the abdominal cavity and around the viscera (block 314). Serial biomarker samples can be obtained from the venous port to track arrest of cellular metabolism (block 320). The standard portal cannula of choice can be inserted into the inferior mesenteric vein or directly into the superior mesenteric/portal vein junction, and the accessory portal perfusion tubing kit attached to the sensor module 114 or run via a separate perfusion line independent of the iOPS. A similar cannulation, perfusion and blood evacuation process can be used for organ donation after cardiac death (DCD) procedures. In the event that abdominal access to the aorta and/or IVC cannot be safely or expeditiously obtained, antegrade cannulation of both the arterial and venous systems can also be performed through a chest incision that accesses the supradiaphragmatic aorta and suprahepatic IVC. Balloon occlusion is performed in the same fashion as previously described.

The processor will compare the fluid color and temperature between the arterial and venous systems until they are substantially equal, as discussed above (block 322). Once equilibrium is reached the preservation is complete, and organ excision can continue (block 324).

The respective catheters can be removed in standard fashion, and the device is discarded. The removable CPU in the sensor module records data for effluent temperature and color. Data may be extracted via one or more of the data ports 232A-C before the device is discarded and the data may be analyzed.

Figure 4:
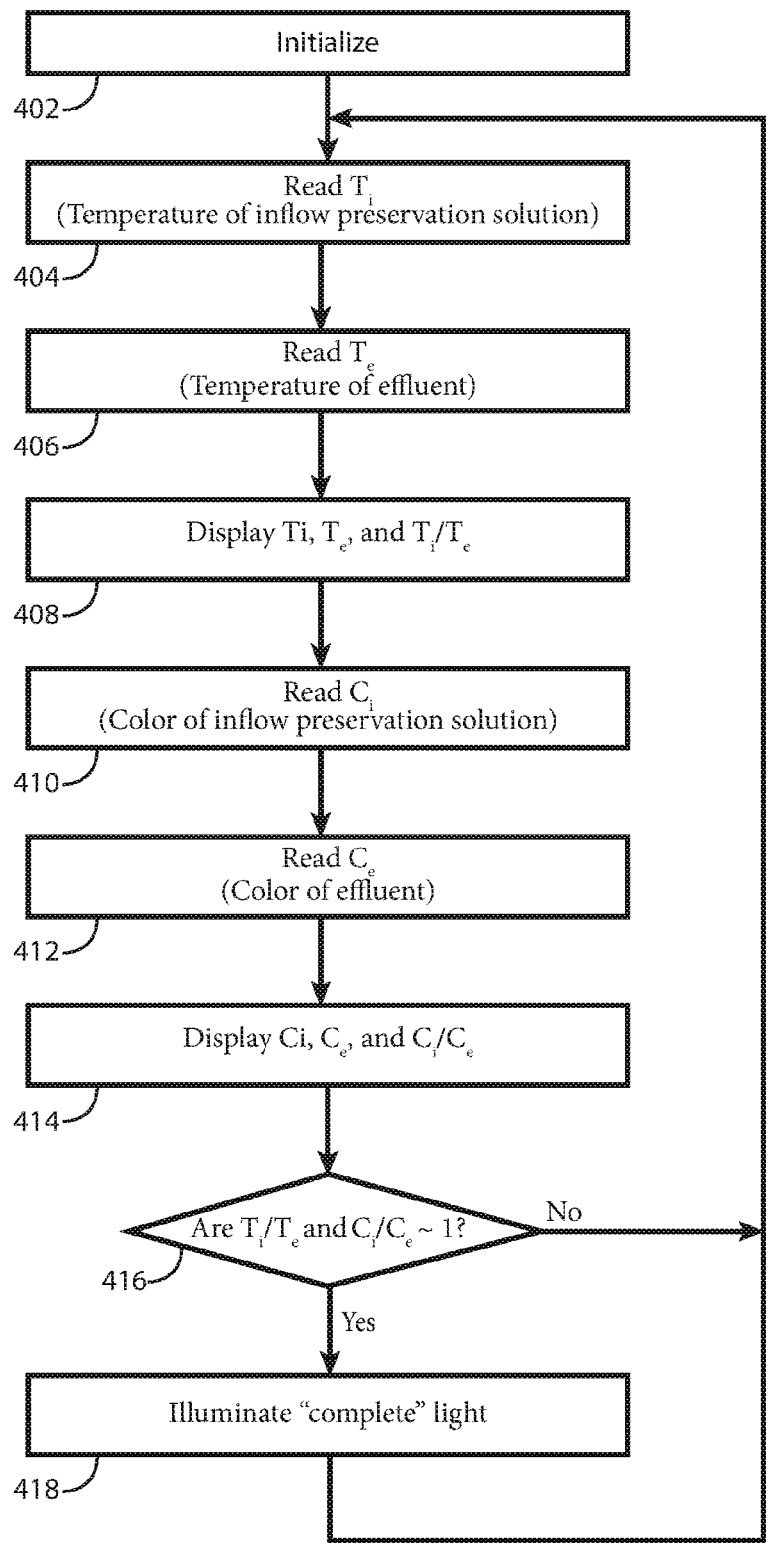
FIG. 4 is a flow chart of the operation of the iOPS.

FIG. 4 is a flow chart of the operation of the iOPS. The processor 210 initializes (block 402). The processor 210 reads $T_i$, the temperature of the inflow preservation solution (block 404). The processor 210 reads $T_e$, the temperature of the effluent (block 406). The processor 210 displays one or more of $T_i$, $T_e$, and $T_i/T_e$ (block 408).

The processor 210 reads $C_i$, the color of the inflow preservation solution (block 410). The processor 210 reads $C_e$, the color of the effluent (block 412). The processor 210 displays one or more of $C_e$, and $C_i/C_e$ (block 414).

The processor then determines if $T_i/T_e$ and $C_i/C_e$ are approximately equal to 1 or if they have plateaued (block 416). If they are ("Yes" branch out of block 416), the processor 210 illuminates the "complete" light (block 418) and returns to block 404. If not ("No" branch out of block 416), the processor returns to block 404. Perfusion and venous effluent evacuation can be discontinued at any time at the surgeon's discretion.

In one aspect, an apparatus includes a sensor module. The sensor module has an arterial catheter connection hub. The sensor module has a perfusion inflow hub coupled through an arterial/portal blood chamber to the arterial catheter connection hub. The sensor module has a venous catheter connection hub. The sensor module has an effluent outflow hub coupled through a venous blood chamber to the venous catheter connection hub. The sensor module has an arterial sensor to sense a parameter of an arterial fluid flowing through the arterial/portal blood chamber. The sensor module has a venous sensor to sense a parameter of a venous fluid flowing through the venous blood chamber. The sensor module has a processor coupled to the arterial sensor and the venous sensor to determine a relationship between the parameter sensed by the arterial sensor and the parameter sensed by the venous sensor.

Implementations may include one or more of the following. The apparatus may include an arterial balloon catheter coupling to the arterial catheter connection hub of the sensor module, and a venous catheter coupling to the venous catheter connection hub of the sensor module. The arterial balloon catheter may include an arterial occlusion balloon and a proximal flange. The arterial balloon catheter may include side holes along a length of the arterial balloon catheter. The arterial balloon catheter may include a catheter tip syringe ball-valve port having a ball valve, and an access port. The venous catheter may include an outer catheter and a fenestrated inner catheter within the outer catheter. The venous catheter may include a venous occlusion balloon. The apparatus may include a source of perfusion fluid coupled to the perfusion hub of the sensor module, and a suction device coupled to the effluent outflow hub of the sensor module. The parameter sensed by the arterial sensor may be a parameter selected from the group of parameters consisting of temperature, color, flow rate, and flow resistance. The parameter sensed by the venous sensor may be a parameter selected from the group of parameters consisting of temperature, color, flow rate, and flow resistance. The processor may determine based on the parameter sensed by the arterial sensor and the parameter sensed by the venous sensor whether a perfusion process involving fluids flowing through the sensor module should be deemed complete. The arterial sensor may include a source of light emitting light into the arterial/portal blood chamber and a light detector to detect light from the arterial/portal blood chamber emitted by the source of light. The venous sensor may include a source of light emitting light into the venous blood chamber and a light detector to detect light from the venous blood chamber emitted by the source of light.

In one aspect, an apparatus includes an arterial catheter. The apparatus includes a venous catheter. The apparatus includes an inflow temperature sensor to sense a temperature inside the arterial catheter. The apparatus includes an outflow temperature sensor to sense a temperature inside the venous catheter. The apparatus includes an inflow color sensor to sense a color inside the arterial catheter. The apparatus includes an outflow color sensor to sense a color inside the venous catheter. The apparatus includes a processor coupled to and receiving signals from the inflow temperature sensor, the outflow temperature sensor, the inflow color sensor, and the outflow color sensor. The apparatus includes a temperature difference display to display a calculated value from the processor representing a relationship between the signal from the inflow temperature sensor and the signal from the outflow temperature sensor. The apparatus includes a color difference display to display a calculated value from the processor representing a relationship between the signal from the inflow color sensor and the signal from the outflow color sensor.

In one aspect, a method includes preparing a body for organ donation. The method includes ligating a distal aorta. The method includes ligating a vena cava. The method includes inserting an arterial catheter into the distal aorta. The method includes inserting a venous catheter into the vena cava. The method includes initiating flow of the preservation solution. The method includes determining, using temperature sensors inserted into the arterial catheter and the venous catheter, that the temperature of the fluid in the arterial catheter is within a temperature threshold of the temperature of the fluid in the venous catheter and, using color sensors inserted into the arterial catheter and the venous catheter, that the color of the fluid in the arterial catheter is within a color threshold of the color of the fluid in the venous catheter, and, as a result, determining that organ excision can begin.

The text above describes one or more specific embodiments of a broader invention. The invention also is carried out in a variety of alternate embodiments and thus is not limited to those described here. The foregoing description of an embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. An apparatus comprising:
   a sensor module comprising:
   a) an arterial catheter connection hub;
   b) a preservation inflow hub coupled through an arterial blood chamber to said arterial catheter connection hub;
   c) a venous catheter connection hub;
   d) an effluent outflow hub coupled through a venous blood chamber to said venous catheter connection hub;
   e) an arterial sensor, a venous sensor, a processor and an input/output device;
   f) said arterial sensor comprising:
      i) a light source configured to emit light into said arterial blood chamber,
      ii) a light detector configured to detect said light in said arterial blood chamber, said light from said light source from said arterial sensor,
      iii) a temperature sensor configured to measure temperature in said arterial blood chamber,
      iv) said arterial sensor configured to measure inflow data comprising light data from said light detector from said arterial sensor and temperature data from said temperature sensor from said arterial sensor of fluid flowing through said arterial blood chamber without direct contact with said fluid flowing through said arterial blood chamber;
   g) said venous sensor comprising:
      i) a light source configured to emit light into said venous blood chamber,
      ii) a light detector configured to detect said light in said venous blood chamber, said light from said light source from said venous sensor,
      iii) a temperature sensor configured to measure temperature in said venous blood chamber, and
      iv) said venous sensor configured to measure effluent data comprising light data from said light detector from said venous sensor and temperature data from said temperature sensor from said venous sensor of fluid flowing through said venous blood chamber without direct contact with said fluid flowing through said venous blood chamber; and
   h) said processor configured to determine a ratio of said inflow data to said effluent data and said input/output device configured to display said ratio, or said inflow data and said effluent data, or a complete message or light when said ratio has reached 1±10%.

2. The apparatus of claim 1, wherein said arterial sensor is further configured to detect flow rate and flow resistance.

3. The apparatus of claim 1, wherein said venous sensor is further configured to detect flow rate and flow resistance.

4. The apparatus of claim 1, further comprising:
   an arterial balloon catheter coupled to said arterial catheter connection hub, and
   a venous catheter coupled to the venous catheter connection hub.

5. The apparatus of claim 4, wherein the arterial balloon catheter comprises:
   an arterial occlusion balloon, and
   a proximal flange.

6. The apparatus of claim 4, wherein said arterial balloon catheter comprises:
   side holes along a length of the arterial balloon catheter.

7. The apparatus of claim 4, wherein said arterial balloon catheter comprises:
   a catheter tip syringe ball-valve port having a ball valve, and
   an access port.

8. The apparatus of claim 4, wherein said venous catheter comprises:
   an outer catheter, and
   a fenestrated inner catheter within said outer catheter.

9. The apparatus of claim 4, wherein said venous catheter comprises:
   a venous occlusion balloon.

10. The apparatus of claim 4, further comprising:
    a source of preservation fluid coupled to said preservation inflow hub, and
    a suction device coupled to the effluent outflow hub.

11. A method of preserving an abdominal organ for donation, said method comprising:
    a) ligating a distal aorta and a vena cava to prepare a body for said donation of said abdominal organ;
    b) using the apparatus of claim 10 and inserting said arterial balloon catheter into said distal aorta in said body for inflow into an abdominal organ in said body;
    c) inserting said venous catheter into said vena cava in said body for outflow from said abdominal organ;
    d) flowing a less than 6° C. preservation solution into said arterial balloon catheter and through the abdominal organ and out said venous catheter to said suction device;
    e) continuing said flowing until said input/output device indicates that said inflow data and effluent data have reached the ratio of 1±10%; and then
    f) excising said abdominal organ for said donation to another person.

* * * * *